US008222242B2

(12) United States Patent
Boss et al.

(10) Patent No.: US 8,222,242 B2
(45) Date of Patent: Jul. 17, 2012

(54) NITRIC OXIDE RELEASING COMPOUNDS

(75) Inventors: Gerry R. Boss, La Jolla, CA (US); Vijay Sharma, Encinitas, CA (US); Kate E. Broderick, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 10 days.

(21) Appl. No.: 12/595,799

(22) PCT Filed: Apr. 10, 2008

(86) PCT No.: PCT/US2008/059947
§ 371 (c)(1),
(2), (4) Date: Mar. 2, 2010

(87) PCT Pub. No.: WO2008/127995
PCT Pub. Date: Oct. 23, 2008

(65) Prior Publication Data
US 2010/0152153 A1    Jun. 17, 2010

(51) Int. Cl.
*A01N 55/02*    (2006.01)
*A61K 31/555*   (2006.01)
*C07B 47/00*    (2006.01)
*C07D 487/22*   (2006.01)

(52) U.S. Cl. ........................................ 514/185; 540/145
(58) Field of Classification Search .................. 540/145; 514/185
See application file for complete search history.

(56) References Cited

OTHER PUBLICATIONS

Sharma et al., Biochemistry, Jul. 2003, vol. 42., No. 29 pp. 8900-8908.*
Freeman et al., Analytica Chimica Acta (1992), 256(2), pp. 269-275.*
Sharma, V.S. et al, "Reactions of Nitric Oxide with Vitamin B12 and Its Precursor, Cobinamide," Biochemistry, Jul. 2003, vol. 42, No. 29, pp. 8900-8908, 9 pages.
PCT International Search Report and Written Opinion, PCT Application No. PCT/US2008/059947, Aug. 20, 2008, 7 pages.

* cited by examiner

*Primary Examiner* — Paul V. Ward
(74) *Attorney, Agent, or Firm* — Fenwick & West LLP

(57) ABSTRACT

Compositions comprising nitrosyl-cobinamide are provided. Also provided are methods for treating hypertension, which comprise administering therapeutically effective amounts of nitrosyl-cobinamide. Also provided are methods for producing nitrosyl-cobinamide.

10 Claims, 10 Drawing Sheets

NITRIC OXIDE RELEASING COMPOUNDS

GOVERNMENT SUPPORT

This invention was made with government support under Grant Nos. 9T32 DK069263, CA118595, CA099835, R21 A164368, and U01 NS58030 awarded by the National Institutes of Health. The government has certain rights in the invention.

CROSS REFERENCE TO RELATED APPLICATIONS

This application claims benefit under 35 U.S.C. §119(e) to U.S. Provisional Application No. 60/911,667 filed Apr. 13, 2007, hereby incorporated by reference in its entirety.

FIELD

The invention relates generally to the field of pharmacology. More specifically, the invention relates to nitric oxide releasing compounds, and methods for the treatment of cardiovascular disease.

BACKGROUND

Various publications, including patents, published applications, technical articles and scholarly articles are cited throughout the specification. Each of these cited publications is incorporated by reference herein, in its entirety.

Nitric oxide (NO)-generating agents induce vasodilatation, and are beneficial in a variety of cardiovascular disorders including angina pectoris, hypertensive emergencies, and congestive heart failure (Elliott W. J. (2004) J. Clin. Hypertension 6:S87-S92; Vaughan C. J., and Delanty N. (2000) Lancet 356:411-417; Teerlink J. R. (2005) Am. J. Cardiol. 96:59 G-67G; Stough W. G. et al. (2005) Amer. J. Cardiology 96:41 G-46G). NO has multiple physiological effects, most notably relaxing vascular smooth muscle cells in both the venous and arterial systems; thus, it is used clinically as both a pre- and after-load reducing agent, and an anti-hypertensive drug (Lloyd-Jones D M et al. (1996) Annu. Rev. Med. 47:365-75). Its major drawback for clinical use is that it is an unstable gas, and, although inhaled NO is used for pulmonary hypertension, administering it presents technical challenges (Haj R M et al. (2006) Curr. Opin. Anaesthesiol. 19:88-95). NO is, therefore, commonly provided as an organic nitrate, such as nitroglycerin (glyceryl trinitrate), isosorbide dintrate, or pentaerythritol tetranitrate. These compounds are thus not pure NO releasing agents, and, at least in the case of nitroglycerin, drug tolerance develops as a consequence of its biotransformation to NO (Sydow K et al. (2004) J. Clin. Invest. 113:482-9; Daiber A et al. (2005) Am. J. Cardiol. 96:25i-36i; and, Parker J D (2004) J. Clin. Invest. 113:352-4). The only direct NO releasing drug clinically available in the United States is sodium nitroprusside, but five cyanide ions are released for every NO molecule, limiting its use because of cyanide toxicity (Schulz V (1984) Clin. Pharmacokinet. 9:239-51; Posner M A et al. (1976) Anesthesiology 44:330-5; Merrifiedl A J B (1974) Br. J. Anaesthesia 46:324). Clearly, better NO-generating drugs are needed (Thatcher G R (2005) Curr. Top. Med. Chem. 5:597-601).

The reactions of NO with cobalamin (vitamin B,2) and cobinamide were recently studied; the latter is a cobalamin precursor lacking a benzimidazole group (Sharma V S et al. (2003) Biochemistry 42:8900-8). The cobalt atom in cobalamin and cobinamide can exist in either a +3 or +2 valency state. Under ambient, oxygen-exposed conditions, the +3 valency state predominates, and cobinamide+3 is refereed to as "cobinamide;" cobinamide+2 is referred to as "Cbi(II)." At neutral pH, NO does not bind to cobinamide, but reduces it to Cbi(II), in the process being oxidized to nitrite; NO then binds with relatively high affinity to Cbi(II) (KA-1010 M'1), yielding nitrosyl-cobinamide (NO-Cbi) (Sharma V S et al. (2003) Biochemistry 42:8900-8). The reaction of NO with Cbi(II) is fully reversible.

SUMMARY

The invention provides novel pharmaceutical compositions that comprise at least one pharmaceutically acceptable carrier and nitrosyl-cobinamide. The compositions further comprise various additives and excipients as described and exemplified herein.

Also featured are methods for preparing nitrosyl-cobinamide. In some aspects, the methods comprise deoxygenating cobinamide, reducing the deoxygenated cobinamide with a weak reducing agent, saturating the reduced cobinamide with NO, and removing unreacted NO. In preferred aspects, the weak reducing agent is deoxygenated ascorbic acid. In some preferred aspects, deoxygenation is effectuated with argon.

The invention also features methods for reducing blood pressure and for treating cardiovascular disorders in a subject. The methods comprise administering to a subject in need of such treatment or in need of a reduction of blood pressure a composition comprising a pharmaceutically acceptable carrier and nitrosyl-cobinamide in an amount effective to treat hypertension or to reduce blood pressure in the subject. The methods further comprise co-administering nitrosyl-cobinamide with another therapeutic agent to a subject in need thereof. Preferably, the subject is a human.

BRIEF DESCRIPTION OF THE DRAWINGS

FIG. 10 shows the effect of oral NO-Cbi on rabbit blood pressure.

DETAILED DESCRIPTION

Figure 1A:
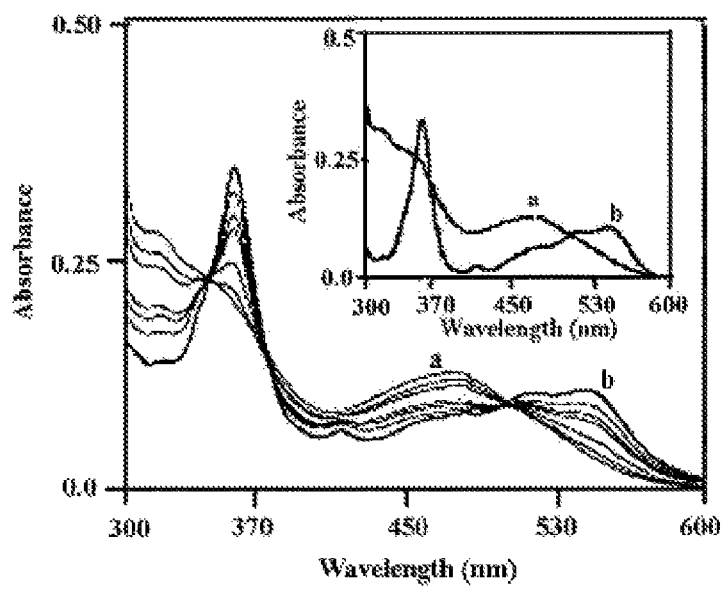
FIGS. 1 (A and B) shows spectrophotometric analysis of NO-Cbi. NO-Cbi was diluted 100-fold into DMEM containing 10% FBS, transferred to a cuvette, and analyzed immediately by spectrophotometry between 300 and 600 nm (curve a). Spectra were obtained every 30 minutes for 3 hours, generating the family of curves, with curve b being the 3 hour spectrum; in the inset, curve b is the spectrum at 16 hours. The cuvette was open to air and kept at room temperature. The same experiment was repeated two times with similar results.

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

The following abbreviations are used throughout the specification: NO, nitric oxide; Cbi, cobinamide; SDS, sodium dodecyl sulfate; FBS, fetal bovine serum; VASP, vasodilator-stimulated phosphoprotein; DMSO, dimethyl sulfoxide.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The terms "treating" or "treatment" refer to any success or indicia of success in the attenuation or amelioration of an injury, pathology or condition, including any objective or subjective parameter such as abatement, remission, diminishing of symptoms or making the injury, pathology, or condition more tolerable to the patient, slowing in the rate of degeneration or decline, making the final point of degeneration less debilitating, improving a subject's physical or mental well-being, or prolonging the length of survival, for example, reducing hypertension. The treatment or amelioration of symptoms can be based on objective or subjective parameters; including the results of a physical examination, neurological examination, and/or psychiatric evaluations.

"Effective amount" or "therapeutically effective amount" are used interchangeably herein, and refer to an amount of a compound, material, or composition, as described herein effective to achieve a particular biological result such as, but not limited to, biological results disclosed, described, or exemplified herein. Such results may include, but are not limited to, the treatment of hypertension in a subject, as determined by any means suitable in the art.

"Pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

Except when noted, "subject" or "patient" are used interchangeably and refer to mammals such as humans and non-human primates, as well as companion, farm, or experimental animals such as rabbits, dogs, cats, rats, mice, horses, cows, pigs, and the like. Accordingly, "subject" or "patient" as used herein means any mammalian patient or subject to which the compositions of the invention can be administered.

"NO-Cbi" refers to the compound nitrosyl cobinamide, having the structure:

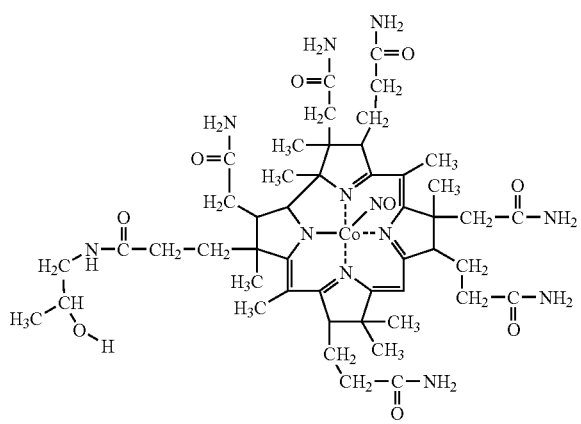

NO-Cbi can be prepared by deoxygenating a cobinamide solution by bubbling argon through it for 5 minutes. Deoxygenated cobinamide is then reduced to Cbi(II) by adding a five-fold molar excess of a weak reducing agent, deoxygenated ascorbic acid. NO gas is bubbled through Cbi(II) for 3 minutes, and removal of excess, unreacted NO is achieved by bubbling argon through the NO-Cbi(II) for 3 minutes. Because the cobinamide is already reduced to Cbi(II) at the time of NO addition, no nitrite formation occurs.

It has been discovered in accordance with the present invention that NO-Cbi is a robust NO donor. It has also been discovered that NO-Cbi releases NO in cultured cells, *Drosophila melanogaster*, mice, and rabbits, rapidly reducing blood pressure in mice and rabbits. Accordingly, the invention features pharmaceutical compositions for the treatment of cardiovascular disorders, such as angina pectoris, hypertension, and for the treatment of acute decompensated congestive heart failure, the compositions comprising NO-Cbi.

I. NO-Cbi Compositions

The NO-Cbi compositions suitable for use in the present invention can be prepared in a wide variety of dosage forms according to any means suitable in the art for preparing a given dosage form. Pharmaceutically acceptable carriers can be either solid or liquid. Non-limiting examples of solid form preparations include powders, tablets, pills, capsules, lozenges, cachets, suppositories, dispersible granules, and the like. A solid carrier can include one or more substances which can also act as diluents, flavoring agents, buffering agents, binders, preservatives, tablet disintegrating agents, or an encapsulating material. Suitable solid carriers include magnesium carbonate, magnesium stearate, talc, sugar, lactose, pectin, dextrin, starch, gelatin, acacia, tragacanth, methylcellulose, sodium carboxymethyl-cellulose, polyethylene glycols, vegetable oils, agar, a low melting wax, cocoa butter, and the like. Non-limiting examples of liquid form preparations include solutions, suspensions, syrups, slurries, and emulsions. Suitable liquid carriers include any suitable organic or inorganic solvent, for example, water, alcohol, saline solution, buffered saline solution, physiological saline solution, dextrose solution, water propylene glycol solutions, and the like, preferably in sterile form.

The compositions can be formulated and administered to the subject as pharmaceutically acceptable salts. Non-limiting examples of pharmaceutically acceptable salts include acid addition salts such as those containing hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate. Such salts can be derived using acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid, according to means known and established in the art.

Aqueous solutions can be prepared by dissolving the active component in water and adding suitable colorants, flavors, stabilizing and thickening agents as desired. Aqueous suspensions can also be made by dispersing the finely divided active component in water with viscous material, such as natural or synthetic gums, resins, methylcellulose, sodium carboxymethylcellulose, and other well-known suspending agents.

Solid forms can be prepared according to any means suitable in the art. For example, capsules are prepared by mixing the composition with a suitable diluent and filling the proper amount of the mixture in capsules. Tablets are prepared by direct compression, by wet granulation, or by dry granulation. Their formulations usually incorporate diluents, binders, lubricants and disintegrators as well as the compound. Non-limiting examples of diluents include various types of starch, cellulose, crystalline cellulose, microcrystalline cellulose, lactose, fructose, sucrose, mannitol, kaolin, calcium phosphate or sulfate, inorganic salts such as sodium chloride and powdered sugar. Powdered cellulose derivatives are also useful. Non-limiting examples of tablet binders include starches, gelatin and sugars such as lactose, fructose, glucose and the like. Natural and synthetic gums are also convenient, including acacia, alginates, methylcellulose, polyvinylpyrrolidone and the like. Polyethylene glycol, ethylcellulose and waxes can also serve as binders.

A lubricant can be used in a tablet formulation to prevent the tablet and punches from sticking in the die. The lubricant can be chosen from such slippery solids as talc, magnesium and calcium stearate, stearic acid and hydrogenated vegetable oils. Tablet disintegrators are substances which swell when wetted to break up the tablet and release the compound, and include starches such as corn and potato starches, clays, celluloses, aligns, gums, methylcellulose, agar, bentonite, wood cellulose, powdered natural sponge, cation-exchange resins, alginic acid, guar gum, citrus pulp, carboxymethyl cellulose, and sodium lauryl sulfate. Tablets can be coated with sugar as a flavor and sealant, or with film-forming protecting agents to modify the dissolution properties of the tablet. The compounds can also be formulated as chewable tablets, by using large amounts of pleasant-tasting substances such as mannitol in the formulation, as is now well-established in the art.

Also included are liquid formulations and solid form preparations which are intended to be converted, shortly before use, to liquid form preparations. Such liquid forms include solutions, suspensions, syrups, slurries, and emulsions. Liquid preparations can be prepared by conventional means with pharmaceutically acceptable additives such as suspending agents (e.g., sorbitol syrup, cellulose derivatives or hydrogenated edible fats or oils); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). These preparations can contain, in addition to the active agent, colorants, flavors, stabilizers, buffers, artificial and natural sweeteners, dispersants, thickeners, solubilizing agents, and the like. The compositions can be in powder form for constitution with a suitable vehicle such as sterile water, saline solution, or alcohol, before use.

Many drugs are present in solution in both the unionized and ionized forms. Generally lipid soluble or lipophilic drugs diffuse most readily across mucosal membranes. Accordingly, the compositions of the present invention can contain buffering agents, pH-adjusting agents, or ionizing agents to adjust the ratio of unionized:ionized forms of the NO-Cbi.

Whether a drug exists in the ionized or non-ionized (unionized) form is largely dependent upon its pKa, and correspondingly on the pH of the solution in which it is dispersed. pKa is defined as the negative logarithm (base 10) of the dissociation constant (Ka). pKa can also be defined as the pH at which a given acid or base is 50% ionized and 50% unionized. Using the well-known Henderson-Hasselbalch equation, concentrations of the charged and uncharged species of a drug can easily be calculated, if the pKa and pH are known. From that equation, it is clear that the ionized portion of the drug will be decreased by lowering the pH for weak acid drugs and increasing the pH for drugs that are weak bases.

Permeability enhancers can significantly enhance the permeability of lipophilic and nonlipophilic drugs. Other penetration enhancers are described in Cooper et al. (1987) "Penetration Enhancers", in Transdermal Delivery of Drugs, Vol. II, Kyodonieus et al., Eds., CRC Press, Boca Raton, Fla. Not all pharmaceutical agents fit this profile, however, and those which do are not always predictably absorbed. Additional forms of chemical enhancers, such as those enhancing lipophilicity, have been developed to improve transport when physically mixed with certain therapeutic agents and provide more predictable absorption. See for example, U.S. Pat. Nos. 4,645,502; 4,788,062; 4,816,258; 4,900,555; 3,472,931; 4,006,218; and 5,053,227. Carriers have also been coupled to pharmaceutical agents to enhance intracellular transport. See Ames et al. (1973) Proc. Natl. Acad. Sci. USA, 70:456-458 and (1988) Proc. Int. Symp. Cont. Rel. Bioact. Mater., 15:142.

Typical permeation enhancers can include bile salts such as sodium cholate, sodium glycocholate, sodium glycodeoxycholate, taurodeoxycholate, sodium deoxycholate, sodium lithocholate chenocholate, chenodeoxycholate, ursocholate, ursodeoxycholate, hydrodeoxycholate, dehydrocholate, glycochenocholate, taurochenocholate, and taurochenodeoxycholate. Other permeation enhancers such as sodium dodecyl sulfate ("SDS"), dimethyl sulfoxide ("DMSO"), sodium lauryl sulfate, salts and other derivatives of saturated and unsaturated fatty acids, surfactants, bile salt analogs, derivatives of bile salts, or such synthetic permeation enhancers as described in U.S. Pat. No. 4,746,508 can be used. It is generally believed that bile salts are good enhancers for hydrophilic drugs and long chain fatty acids, their salts, derivatives, and analogs are more suitable for lipophilic drugs. DMSO, SDS, and medium chain fatty acids (about C-8 to about C-14) their salts, derivatives, and analogs may work for both hydrophilic and lipophilic drugs.

The permeation enhancer concentration within the dissolvable matrix material can be varied depending on the potency of the enhancer and rate of dissolution of the dissolvable matrix. Other criteria for determining the enhancer concentration include the potency of the drug and the desired lag time. The upper limit for enhancer concentration is set by toxic effect to or irritation limits of the mucosal membrane.

As mentioned previously, the compositions can also include a disintegrating agent. Tablet disintegrators are substances which swell when wetted to break up the tablet and release the compound, and include starches such as corn and potato starches, clays, celluloses, aligns, gums, methylcellulose, agar, bentonite, wood cellulose, powdered natural sponge, cation-exchange resins, alginic acid, sodium alginate, guar gum, citrus pulp, carboxymethyl cellulose, polyvinylpyrrolidone, and sodium lauryl sulfate. Acrylic type polymers can also advantageously be used as disintegrators, including methacrylic copolymers of type C (as disclosed in U.S. Pat. No. 6,696,085).

II. Administration of NO-Cbi Compositions

The compositions can be formulated for use in topical administration. Such formulations include, e.g., liquid or gel preparations suitable for penetration through the skin such as creams, liniments, lotions, ointments or pastes, and drops suitable for delivery to the eye, ear or nose.

In some aspects, the present compositions include creams, drops, liniments, lotions, ointments and pastes are liquid or semi-solid compositions for external application. Such compositions can be prepared by mixing the active ingredient(s) in powdered form, alone or in solution or suspension in an aqueous or non-aqueous fluid with a greasy or non-greasy base. The base can comprise complex hydrocarbons such as glycerol, various forms of paraffin, beeswax; a mucilage; a mineral or edible oil or fatty acids; or a macrogel. Such compositions can additionally comprise suitable surface active agents such as surfactants, and suspending agents such as agar, vegetable gums, cellulose derivatives, and other ingredients such as preservatives, antioxidants, and the like.

The compositions can also be formulated for injection into the subject. For injection, the compositions of the invention can be formulated in aqueous solutions such as water or alcohol, or in physiologically compatible buffers such as Hanks's solution, Ringer's solution, or physiological saline buffer. The solution can contain formulatory agents such as suspending, stabilizing and/or dispersing agents. Injection formulations can also be prepared as solid form preparations which are intended to be converted, shortly before use, to liquid form preparations suitable for injection, for example, by constitution with a suitable vehicle, such as sterile water, saline solution, or alcohol, before use.

The compositions can also be formulated in sustained release vehicles or depot preparations. Such long acting formulations can be administered by implantation (for example subcutaneously or intramuscularly) or by intramuscular injection. Thus, for example, the compositions can be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well-known examples of delivery vehicles suitable for use as carriers for hydrophobic drugs.

Administration of the compositions can be by infusion or injection (intravenously, intramuscularly, intracutaneously, subcutaneously, intrathecal, intraduodenally, intraperitoneally, and the like). The compositions can also be administered intranasally, vaginally, rectally, orally, or transdermally. Preferably, the compositions are administered intravenously. Administration can be at the direction of a physician.

For buccal administration, the compositions can take the form of tablets, troche or lozenge formulated in conventional manner. Compositions for oral or buccal administration, can be formulated to give controlled release of the active compound. Such formulations can include one or more sustained-release agents known in the art, such as glyceryl mono-stearate, glyceryl distearate and wax.

Compositions can be applied topically. Such administrations include applying the compositions externally to the epidermis, the mouth cavity, eye, ear and nose. This contrasts with systemic administration achieved by oral, intravenous, intraperitoneal and intramuscular delivery. Compositions for use in topical administration include, e.g., liquid or gel preparations suitable for penetration through the skin such as creams, liniments, lotions, ointments or pastes, and drops suitable for delivery to the eye, ear or nose.

Compositions can be administered by inhalation. Compositions can be inhaled through the nose or mouth. In some aspects of the invention, inhalation can occur via a nasal spray, dry powder inhaler, metered-dose inhaler, vaporizer, and nebulizer.

Various alternative pharmaceutical delivery systems may be employed. Non-limiting examples of such systems include liposomes and emulsions. Certain organic solvents such as dimethylsulfoxide can also be employed. Additionally, the compounds can be delivered using a sustained-release system, such as semipermeable matrices of solid polymers containing the therapeutic agent. The various sustained-release materials available are well known by those skilled in the art. Sustained-release capsules can, depending on their chemical nature, release the compounds over a range of several days to several weeks to several months.

III. Methods of Treatment

The invention also features methods for treating cardiovascular disorders, such as angina pectoris, hypertension, and for the treatment of acute decompensated congestive heart failure, in a subject. For example, in one aspect of the invention hypertension can be treated. Preferably, the methods are amendable for treating acute/malignant hypertension (arteriolar nephrosclerosis). In one preferred aspect, a subject with malignant hypertension is identified and treated with a composition comprising NO-Cbi as described herein.

The inventive methods are amenable to treating hypertension of any origin, including but not limited to renal hypertension, adrenal gland tumors, coarctation of the aorta, the metabolic syndrome and obesity, pregnancy, alcohol abuse, heart disease, essential hypertension, and the like. The methods are also amenable to treating other cardiovascular disorders, such as angina pectoris and congestive heart failure, as administration of NO-Cbi will significantly reduce the workload on the heart and reduce return blood flow to the heart, because NO is both an after-load reducing agent, i.e., it lowers blood pressure by dilating arteries, and a pre-load reducing agent, i.e., it reduces the amount of blood returning to the heart by dilating veins.

To treat hypertension in a subject, a therapeutically effective amount of NO-Cbi is administered to the subject. A therapeutically effective amount will provide a clinically significant decrease in blood pressure, among other things.

The effective amount of the composition to be administered can be dependent on any number of variables, including without limitation, the species, breed, size, height, weight, age, overall health of the subject, the type of formulation, the mode or manner or administration, or the severity of the high blood pressure. The appropriate effective amount can be routinely determined by those of skill in the art using routine optimization techniques and the skilled and informed judgment of the practitioner and other factors evident to those skilled in the art. Preferably, a therapeutically effective dose of the compounds described herein will provide therapeutic benefit without causing substantial toxicity to the subject.

Toxicity and therapeutic efficacy of agents or compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Agents or compositions which exhibit large therapeutic indices are preferred. The data obtained from cell culture assays and animal studies can be used in formulating a range of dosage for use in the subject. The dosage of such agents or compositions lies preferably within a range of circulating concentrations that include the ED50 with little or no toxicity. The dosage can vary within this range depending upon the dosage form employed and the route of administration utilized.

For any composition used in the methods of the invention, the therapeutically effective dose can be estimated initially from in vitro assays such as cell culture assays. For example, a dose can be formulated in animal models to achieve a circulating plasma concentration range that includes the IC50 as determined in cell culture (i.e., the concentration of the composition which achieves a half-maximal reduction in blood pressure). Such information can be used to more accurately determine useful doses in a specified subject such as a human. The treating physician can terminate, interrupt, or adjust administration due to toxicity, or to organ dysfunctions, and can adjust treatment as necessary if the clinical response were not adequate in order to improve the response. The magnitude of an administered dose in the management of hypertension will vary with the severity of hypertension to be treated and the route of administration. The severity of hypertension can, for example, be evaluated, in part, by standard prognostic evaluation methods.

In one aspect of the inventive methods, the compositions comprise a concentration of NO-Cbi in a range of about 0.01% to about 90% of the dry matter weight of the composition. In some aspects, NO-Cbi comprises up to about 50% of the dry matter weight of the composition. In some aspects, NO-Cbi comprises up to about 40% of the dry matter weight of the composition. In some aspects, NO-Cbi comprises up to about 30% of the dry matter weight of the composition. In some aspects, NO-Cbi comprises up to about 25% of the dry matter weight of the composition. In some aspects, NO-Cbi comprises up to about 20% of the dry matter weight of the composition. In some aspects, NO-Cbi comprises up to about 15% of the dry matter weight of the composition. In some aspects, NO-Cbi comprises up to about 10% of the dry matter weight of the composition.

In some aspects, subjects can be administered NO-Cbi in a daily dose range of about 0.001 mg/kg to about 10 mg/kg of the weight of the subject. The dose administered to the subject can also be measured in terms of total amount of drug administered per day. In some aspects, a subject is administered about 0.01 to about 500 milligrams of NO-Cbi per day. In some aspects, a subject is administered up to about 0.05 milligrams of NO-Cbi per day. In some aspects, a subject is administered up to about 0.1 milligrams of NO-Cbi per day. In some aspects, a subject is administered up to about 0.5 milligrams of NO-Cbi per day. In some aspects, a subject is administered up to about 1 milligrams of NO-Cbi per day. In some aspects, a subject is administered up to about 5 milligrams of NO-Cbi per day. In some aspects, a subject is administered up to about 10 milligrams of NO-Cbi per day. In some aspects, a subject is administered up to about 25 milligrams of NO-Cbi per day. In some aspects, a subject is administered up to about 50 milligrams of NO-Cbi per day. In some aspects, a subject is administered up to about 100 milligrams of NO-Cbi per day. In some aspects, a subject is administered up to about 150 milligrams of NO-Cbi per day. In some aspects, a subject is administered up to about 200 milligrams of NO-Cbi per day.

Treatment can be initiated with smaller dosages that are less than the optimum dose of NO-Cbi, followed by an increase in dosage over the course of the treatment until the optimum effect under the circumstances is reached. If needed, the total daily dosage can be divided and administered in portions throughout the day.

For effective treatment of hypertension, one skilled in the art can recommend a dosage schedule and dosage amount adequate for the subject being treated. It may be preferred that dosing occur one to four or more times daily for as long as needed. The dosing can occur less frequently if the compositions are formulated in sustained delivery vehicles. The dosage schedule can also vary depending on the active drug concentration, which can depend on the needs of the subject.

The compositions of the invention for treating hypertension can also be co-administered with other therapeutic agents that are selected for their particular usefulness against the condition that is being treated. For example, such therapeutic agents can be pain relievers, blood thinners/anticoagulants, clot busters, stomach antacids, compounds which lessen untoward effects of the compositions, other known agents that lower blood pressure. The compositions can be co-administered with cobalamin (vitamin B12) to reduce or eliminate potential toxicity of the administered cobinamide.

The administration of these additional compounds can be simultaneous with the administration of NO-Cbi, or can be administered in tandem, either before or after the administration of NO-Cbi, as necessary. Any suitable protocol can be devised whereby the various compounds to be included in the combination treatment are administered within minutes, hours, days, or weeks of each other. Repeated administration in a cyclic protocol is also contemplated to be within the scope of the present invention.

The following Exemplary Aspects of specific examples for carrying out the present invention are offered for illustrative purposes only, and are not intended to limit the scope of the present invention in any way.

IV. Exemplary Aspects

Example 1

NO-Cbi Synthesis

Cobinamide was synthesized from hydroxocobalamin as described in Broderick (Broderick K E et al. (2005) J. Biol. Chem. 280:8678-85). At neutral pH, it exists as aquo-hydroxocobinamide. NO gas, >99.5% pure, was from Matheson Tri-gas. NO was bubbled through 1 M NaOH immediately prior to use to remove potential oxidized forms of NO. CS-54 rat pulmonary artery smooth muscle cells were from A. Rothman (Idrsiss S D et al. (1999) J. Biol. Chem. 274:9489-93); they maintain a differentiated phenotype through multiple subcultures. Canton-S *Drosophila melanogaster* were from the Bloomington Stock Center, and 10-12 wk old male C57BL/6J mice were from Jackson Laboratories. Mice were fed Teklad 7001 standard diet, and were studied according to NIH Guidelines for the Care and Use of Laboratory Animals approved by the Institutional Animal Care and Use Committee of the VA San Diego Healthcare System. The NO-releasing agents Deta-NONOate and spermine NONOate were from Cayman Chemicals, nitroglycerin was from American Regent Laboratories, and the membrane-permeable cGMP analog 8-CPT-cGMP was from Biolog.

NO-Cbi was prepared fresh daily as described by Sharma (Sharma V S et al. (2003) Biochemistry 42:8900-8). Briefly, a 4-8 mM cobinamide solution was placed in a stoppered tube, and deoxygenated by bubbling argon through it for 5 minutes; it was then reduced to Cbi(II) by adding a five-fold molar excess of a weak reducing agent, deoxygenated ascorbic acid. NO gas was bubbled through the Cbi(II) for 3 minutes, and excess unreacted NO was removed by bubbling argon through the NO-Cbi(II) for 3 minutes. Because the cobinamide was already reduced to Cbi(II) at the time of NO addition, no nitrite was formed.

Example 2

Spectral Analyses and Mass Spectrometry

NO-Cbi was diluted 100-fold in water, PBS, or DMEM containing 10% FBS to a final concentration of 50 uM. It was analyzed spectrophotometrically between 300 and 600 nm in a Kontron 860 spectrophotometer, and by mass spectroscopy using a LCQ classic ion-trap-type mass spectrometer (Thermo-Finnigan) at 160° C. capillary temperature and 5000V spray voltage. The mass spectrometry data were acquired in profile mode and analyzed on Xcalibur software.

Example 3

Measurement of VASP Phosphorylation

VASP is phosphorylated in response to NO activation of the heme-containing enzyme soluble guanylate cyclase: the increased cGMP activates PKG, which phosphorylates VASP preferentially on serine 259 (Butt E et al. (1994) J. Biol. Chem. 269:14509-17). VASP phosphorylation has been used as a measure of NO availability (Zhuang S et al. (2004) J. Biol. Chem. 279:10379-10407; and, Ibarra-Alvarado C et al. (2002) Mol. Pharmacol. 61:312-9). Briefly, cells treated with an NO-releasing agent were extracted rapidly in a sodium dodecyl sulfate (SDS) containing sample buffer, and the cell extracts were subjected to SDS-polyacrylamide gel electrophoresis. Phospho-VASP was assessed by immunoblotting using an antibody specific for VASP phosphorylated on Ser259 (Smolenski A et al. (1998) J. Biol. Chem. 273:20029-35).

Example 4

Measurement of Nitrite and Nitrate

NO has a short half life, being oxidized to nitrite and nitrate in the presence of oxygen. Measuring nitrite and nitrate is, therefore, a common method for assessing NO production (Idrsiss S D et al. (1999) J. Biol. Chem. 274:9489-93). Nitrite and nitrate were measured in CS-54 cell extracts and fly extracts using a kit from Active Motif based on an enhanced Griess reagent, as described previously (Broderick K E et al. (2006) FASEB J. 20:1865-73).

Example 5

Measurement of Malpighian Tubule Secretion

Malpighian tubules are the osmoregulatory organs of *D. melanogaster*, corresponding to vertebrate kidneys. Tubular fluid secretion is stimulated by NO and cGMP, and fluid secretion rates were measured as described previously (Broderick K E et al. (2005) J. Biol. Chem. 280:8678-85). Briefly, the Malpighian tubule pair of a fly was resected and suspended in mineral oil. The proximal end of the tubule was bathed in half-strength Schneiders insect medium, to which could be added a secretagogue, and fluid secretion rates were assessed by measuring the size of drops formed at the ureteral end of the tubule.

Example 6

Injection of *D. melanogaster*

Flies were injected into the thorax with 1 ul of fluid using a 33 gauge needle attached to a 2.5 ul syringe as described previously (Broderick K E et al. (2006) FASEB J. 20:1865-73). The fluid volume of a fly is ~10 ul, and thus, the injected agent was diluted about 10-fold. The flies were observed for activity for the following 48 h; flies motionless for more than 5 minute were scored as dead.

Example 7

Measurement of Mouse Blood Pressure

Pulse, and systolic and diastolic blood pressures, were measured non-invasively in the tail artery of mice by restraining mice on a warming platform maintained at ~38° C. The base of the tail was placed in a computer-controlled pneumatic cuff, and the distal tail was placed in a sensor assembly consisting of a light emitting diode and a photodiode detector. Baseline measurements were made with the mice awake in a dark chamber. The mice were then anesthetized with 3% isoflurane in an induction chamber, and returned to the platform where they received 1.5% isoflurane with 2 liter per minute of oxygen via a nose cone; the isoflurane caused a small, but stable, drop in blood pressure. Drugs in a volume of 100 ul were injected intraperitoneally into the mice, and pulse and blood pressure were measured every 5-15 minute, taking five readings at each time point.

Example 8

Statistical Analyses

Unless stated otherwise, differences between groups were analyzed by a one-way ANOVA with a Dunnett's post-test comparison to the control group.

Example 9

Analysis and Stability of NO-Cbi

To confirm NO-Cbi synthesis, the product was analyzed by spectrophotometry and mass spectrometry. The spectral analysis from 300 to 600 nm resembled that of Cbi(II), and was identical to the spectrum of NO-Cbi published previously (FIG. 1) (Sharma V S et al. (2003) Biochemistry 42:8900-8). The mass spectrum of NO-Cbi showed a species with a mass of 1037 Da, not present in the spectrum of Cbi(II), which had a mass of 1025 Da; the difference corresponds to replacement of a water molecule on Cbi(II) by an NO group.

For NO-Cbi to be useful as a drug, it needs to be relatively stable in aqueous solution. From previous work, it was known that the half-life of NO-Cbi is short when it is incubated with excess heme; the latter binds NO tightly, and will effectively remove NO from solution (Sharma V S et al. (2003) Biochemistry 42:8900-8). In addition to defining the kinetics of NO-Cbi dissolution, these studies showed that NO-Cbi's primary break down products are NO and Cbi(II): NO–Cbi*NO+Cbi (II).

Figure 1B:
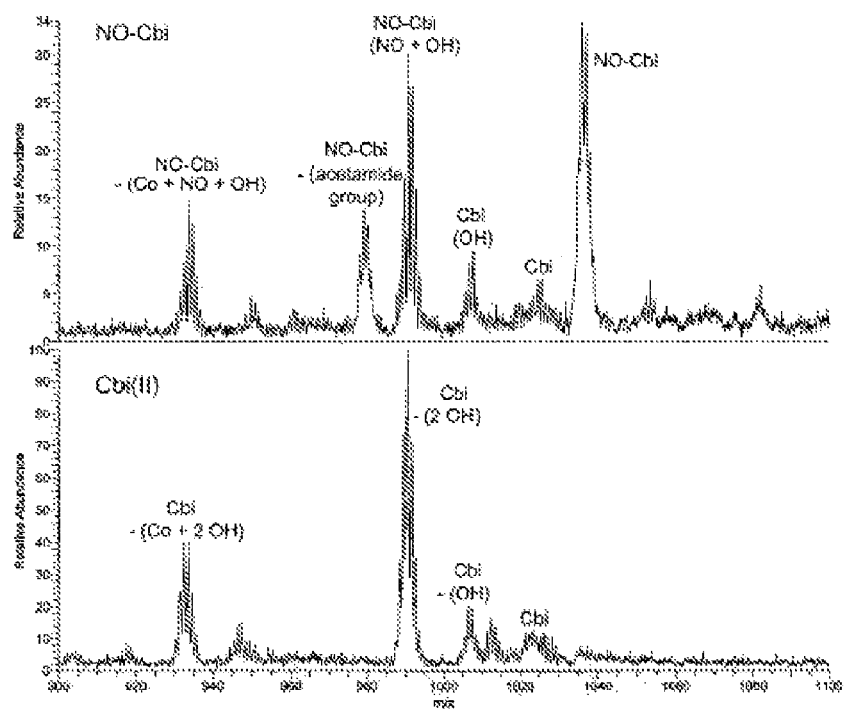

In the absence of an added NO scavenger, NO-Cbi was remarkably stable: its spectrum did not change over 16 hours when kept at room temperature in water, and little spectral change occurred in phosphate-buffered saline (PBS). These studies were conducted with samples open to air, indicating that the back reaction of NO with Cbi(II) is much faster than NO's reaction with oxygen or Cbi(II) oxidation to cobinamide. When NO-Cbi was added to Dulbecco's minimal essential medium (DMEM) containing 10% fetal bovine serum (FBS), its spectrum changed to that of cobinamide over about 3 h, yielding a half-life of-90 minute (FIG. 1). These data suggest that NO released from NO-Cbi reacted with a constituent of the culture medium not present in water or PBS. NO reacts readily with sulfhydryl groups in the presence of oxygen (Kharitonov V G et al. (1995) J. Biol. Chem. 270:28158-64), suggesting it was reacting with cysteines in the culture medium, and we found that adding 1 mM cysteine to PBS significantly reduced NO-Cbi's half-life. Thus, NO-Cbi is stable in aqueous solutions exposed to air, but, in the presence of an NO-reactive species such as heme or a sulfhydryl group, it breaks down relatively quickly; the resulting free Cbi(II) is oxidized to cobinamide.

Example 10

Effect of NO-Cbi on Cultured Cells

Figure 2A:
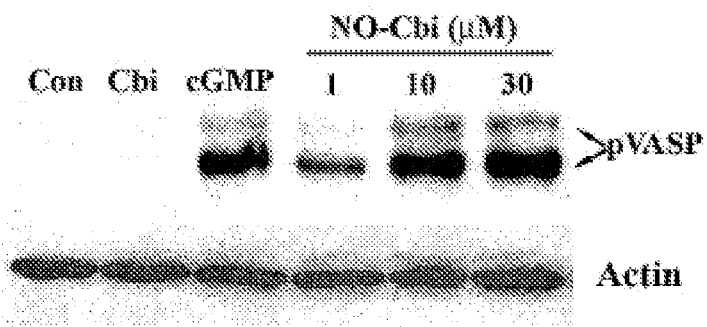
FIG. 2 shows the effect of NO-Cbi on cultured cells. CS-54 rat vascular smooth muscle cells were treated with the indicated concentrations of NO-Cbi for 1 hour (A), or 10 μM NO-Cbi for the indicated times (B and C). A and B. The cells were extracted in situ, and the extracts were subjected to SDS-polyacrylamide gel electrophoresis, followed by immunoblotting with antibodies specific for vasodilator-stimulated phosphoprotein (VASP) phosphorylated on Ser239 (upper blots), and actin as a loading control (lower blots). Dual bands of phosphorylated VASP occur because VASP can be phosphorylated on Ser157 in addition to Ser239; the former phosphorylation causes the protein to migrate with a slightly higher apparent molecular mass. (C) Cell extracts were clarified by centrifugation, and nitrite and nitrate in the extracts were measured by an enhanced Griess reagent method. In A and B, "Con" refers to control, which was cells treated with water. As indicated, the effects of 30 μM cobinamide (Cbi) and 100 μM 8-CPT-cGMP (cGMP) are shown for comparison. In A and B, similar results were obtained in two other experiments. In C, results are the mean±SEM of three independent experiments; the 1, 2, 3, 4, and 5 hours time points for the NO-Cbi-treated samples were statistically different from the control samples (p<0.05).

To determine if NO released from NO-Cbi can have a physiologic effect in cultured cells, vasodilator-stimulated phosphoprotein (VASP) phosphorylation was assessed in CS-54 cells. VASP is phosphorylated under conditions of increased NO and increased cGMP, and since CS-54 cells are vascular smooth muscle cells, they are a good model for studying NO effects (Zhuang S et al. (2004) J. Biol. Chem. 279:10379-10407; and, Ibarra-Alvarado C et al. (2002) Mol. Pharmacol. 61:312-9). It was observed that over a concentration range from 1 to 30 i_μM, NO-Cbi induced VASP phosphorylation, and 10 μM NO-Cbi yielded similar results as 100 i_1M 8-CPT-cGMP (FIG. 2a). The effect of NO-Cbi could be observed at 15 minutes, was maximal at 30-60 minutes, and declined over the ensuing 4 hours (FIG. 2b).

Figure 2B:
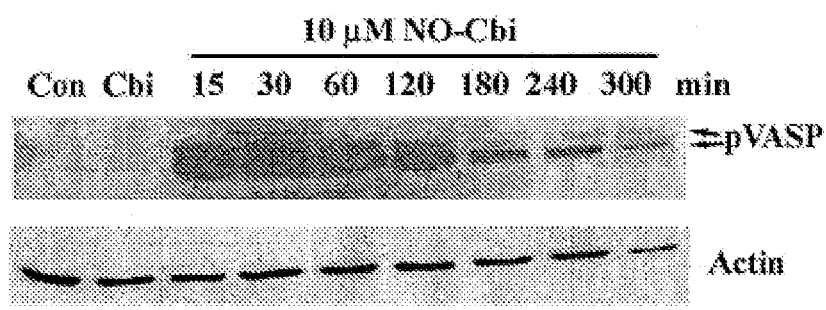
Figure 2C:
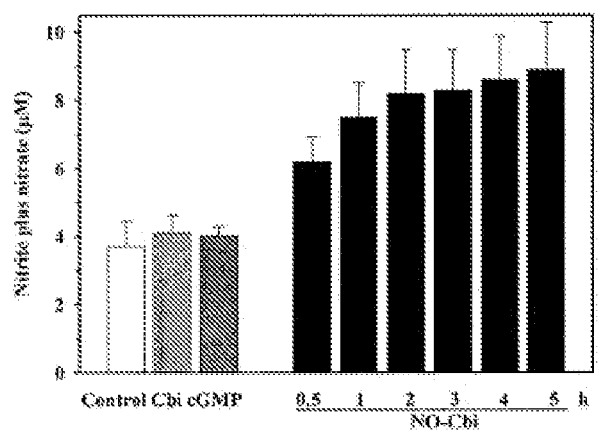

NO release by NO-Cbi was confirmed by showing increased nitrite and nitrate in the culture medium of NO-Cbi-treated cells (FIG. 2c). The increased amount of nitrite and nitrate accounted for 55% of the amount of NO added to the cells as NO-Cbi. This suggests the NO-Cbi either did not break down entirely to NO and Cbi(II) or that a substantial amount of NO was lost; NO could diffuse out of the medium into the surrounding air or react with heme- or sulfhydryl-containing compounds in the cells or medium. Because the nitrite/nitrate levels showed minimal increase after 3 hours, it would appear that all of the NO-Cbi broke down, but that some NO was lost. Previous work showing that NO-Cbi breaks down rapidly in the presence of heme (Sharma V S et al. (2003) Biochemistry 42:8900-8), and the present studies showing that NO released from NO-Cbi reacts readily with cysteine, are also consistent with this explanation. Measuring nitrite and nitrate accumulation also provided an estimate of the half-life of NO-Cbi, which was calculated to be between 30 minutes and 1 hour.

Neither cobinamide, Cbi(II), or ascorbate had any effect on VASP phosphorylation or nitrite/nitrate levels when added to CS-54 cells (FIGS. 2a-c; only cobinamide data are shown).

Example 11

Effect of NO-Cbi on D. melanogaster Malpighian Tubule Secretion

Figure 3:
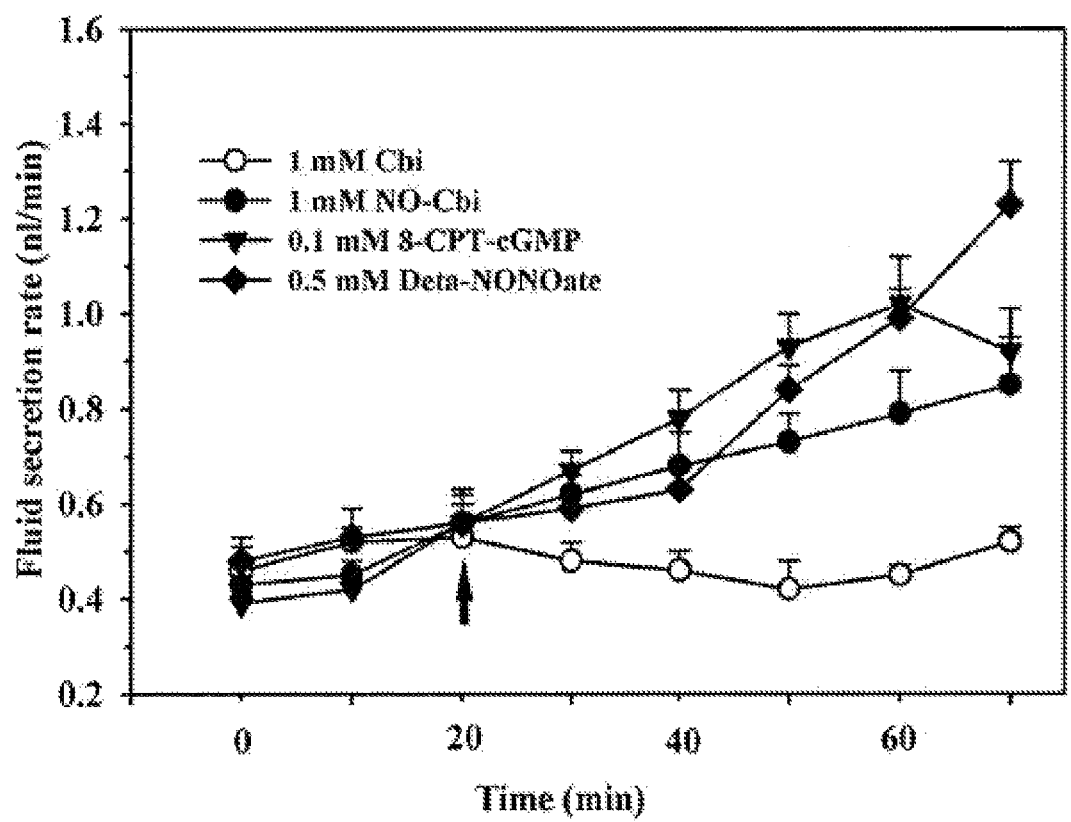
FIG. 3 shows the effect of NO-Cbi in *D. melanogaster*. (A) Tubular secretion rates of Malpighian tubules isolated from *D. melanogaster* were measured, using half-strength Schneider's medium. Basal tubular secretion was measured at 0, 10, and 20 minutes; at 20 minutes (depicted by the arrow) 1 mM cobinamide (Cbi, open circles), 1 mM NO-Cbi (filled circles), 0.5 mM Deta-NONOate (diamonds), or 100 μM 8-CPT-cGMP (inverted triangles) were added. Results are the mean±S.D. of three independent experiments performed on Malpighian tubule pairs from 10 flies. At the 70 minute time point (i.e., 50 minutes after adding drugs), rates of tubular secretion were 1.6 times higher in the NO-Cbi-treated tubules than in the cobinamide-treated tubules (p<0.01 for the difference between the two groups using a one-tailed t test). (B). Flies were injected with 1 μl of 1 mM cobinamide (Cbi, open circles), 1 mM NO-Cbi (filled circles), 0.5 mM Deta-NONOate (diamonds), or 1 mM spermine NONOate (squares). At the indicated times, the flies were observed for activity, and flies that were motionless for >5 minutes were scored as dead. The data are plotted as a Kaplan-Meier survival curve, and are the mean±SD of three experiments, with 10 flies per condition per experiment. A log rank test analysis yielded a p value of 0.0011 for the comparison between NO-Cbi- and cobinamide-treated flies. (C). Flies were injected with 1 μl of water (control, open bar), 1 mM cobinamide (Cbi, grey bar), or 1 mM NO-Cbi (black bars). Flies were killed and extracts were prepared at 3 hours for the water- and cobinamide-injected flies, and at the indicated times for the NO-Cbi-injected flies. Nitrite and nitrate in the extracts were measured using an enhanced Griess reagent. Data are the mean±SEM of three experiments performed on five flies per condition per experiment; the values at 1, 2, and 3 hours post NO-Cbi injection were significantly different from the control group (p<0.01). In all three panels, 1 mM Cbi(II) and 5 mM ascorbic acid yielded similar results as 1 mM cobinamide.

Malpighian tubules are an excellent model for studying the effects of a drug on an intact organ system (Broderick K E et al. (2003) Am. J. Physiol. Cell Physiol. 285:C1207-18). It was found that 1 mM NO-Cbi stimulated fluid secretion to a similar extent as 100 μM 8-CPT-cGMP, but somewhat less than 500 μM Deta-NONOate, which releases two NO molecules (FIG. 3a). The reason for the lesser efficacy of NO-Cbi compared to Deta-NONOate is likely related to cysteine in the Schneiders medium bathing the tubules; no effect of NO-Cbi was observed at full strength of Schneider's medium, and lower concentrations than half-strength Schneiders did not support tubule secretion. Deta-NONOate may not be affected as much by cysteine in the medium, because it has a slower NO release rate and the intact drug can be transported intracellularly before much NO is released. Neither cobinamide nor Cbi(II) significantly affected tubular secretion (FIG. 3a).

Example 12

Effect of NO-Cbi on D. melanogaster Viability

It was showed previously that NO is lethal to D. melanogaster, and that NO produced in a fly model of sepsis contributes to fly mortality (Broderick K E et al. (2006) FASEB J. 20:1865-73). Injecting 1 μl of 1 mM NO-Cbi into D. melanogaster killed the flies as effectively as 1 mM spermine NONOate, which has a half-life of-45 minute, and more rapidly, and more effectively, than 0.5 mM Deta-NONOate (FIG. 3b; Deta-NONOate has a relatively long half-life of ~50 h). Faster NO release by NO-Cbi and spermine NONOate, compared to Deta-NONOate, may have contributed to their increased fly killing, since brisk release could overwhelm the flies ability to oxidize NO to nitrite and nitrate. As observed previously (Broderick K E et al. (2006) FASEB J. 20:1865-73), cobinamide was not toxic to flies, and neither was Cbi(II) (FIG. 3b; data are shown only for cobinamide).

Nitrite and nitrate in extracts of NO-Cbi-injected flies were measured, and, as in the studies with CS-54 cells, a little over 50% of the injected NO as nitrite and nitrate was recovered (FIG. 3c). The nitrite/nitrate levels reached a maximum at 1 hour, and returned to that of water-injected flies at 4-5 hours (FIG. 3c). This suggests the flies were excreting nitrite and nitrate, making it difficult to estimate a half-life. Nitrite and nitrate excretion likely explained the only partial recovery of NO.

Example 13

Effect of NO-Cbi on Blood Pressure and Heart Rate in Mice

Figure 4A:
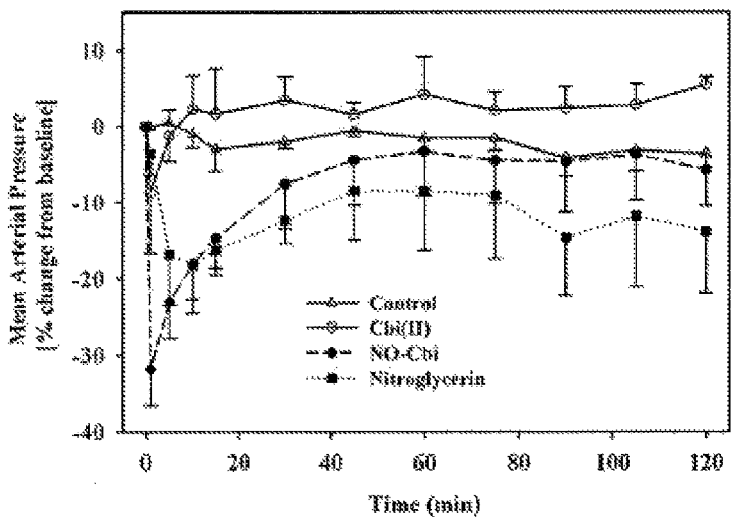
FIG. 4 shows the effect of NO-Cbi on blood pressure and heart rate in mice. Mice were anesthetized with 1.5% isoflurane gas, and after achieving a stable blood pressure and pulse (about 10 minutes), they were injected intraperitoneally with 100 μl of (Need a space between the 1 and the o) 8 mM Cbi(II) (open circles, solid line), 8 mM NO-Cbi (filled circles, dashed line), or 8 mM nitroglycerin (squares, dotted lines) (panels a and b). Control refers to anesthetized mice who received 100 μl water (triangles, solid line). In panel C, 100 μl of 6 mM NO-Cbi was injected at 0, 32, and 64 minutes as indicated by the arrows. Systolic and diastolic blood pressures, and pulse rate, were measured at the indicated times on the tail artery using a non-invasive tail cuff. The percent change in mean arterial pressure (A and C), and pulse rate (B and C) are shown. For panels A and B, data are the mean±SD of results from five mice for NO-Cbi studied on separate days, and four mice for the other conditions. The blood pressure and pulse rate for the NO-Cbi-treated mice were significantly different (p<0.01) from that of the control mice when assessed at 1 and 15 minutes, respectively. Data in panel C are the mean±SD of results from three mice studied on different days.

To determine the effect of NO release from NO-Cbi in an intact mammal, blood pressure and pulse of mice injected intraperitoneally with NO-Cbi were measured. It was observed that 0.8 μmol NO-Cbi rapidly reduced the systolic and diastolic blood pressure of mice, and that ~45 minutes was required for the blood pressure to return to control values (FIG. 4a; only the mean arterial pressure is shown). NO-Cbi reduced blood pressure more potently than an equimolar amount of nitroglycerin (FIG. 4a; the late decrease in blood pressure by nitroglycerin may be because the drug can potentially release three NO molecules with different kinetics).

Figure 4B:
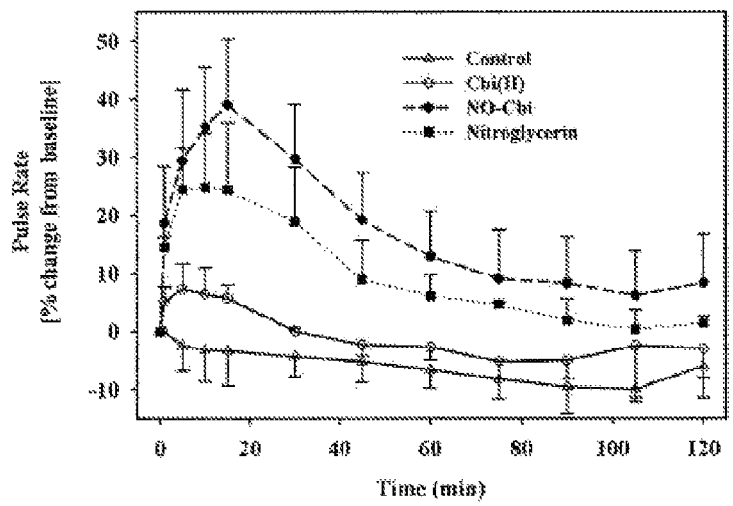

Concomitantly with the decreased blood pressure, pulse rates of the mice increased, and again, the effect of NO-Cbi was more pronounced than that observed with nitroglycerin (FIG. 4b). For NO-Cbi, pulse rates remained more than 10% above control values until 75 minutes; this suggests that NO continued to be released until about this time, and that the mice compensated for NO-induced hypotension by a reflex tachycardia. Cobinamide, Cbi(II), and ascorbate had no significant effect on blood pressure or heart rate (FIGS. 4a and b; only the data for Cbi(II) are shown). Because of the compensatory tachycardia, it is difficult to estimate the half-life of NO-Cbi in the mice, but it appeared to be between 30 and 60 minutes.

Figure 4C:
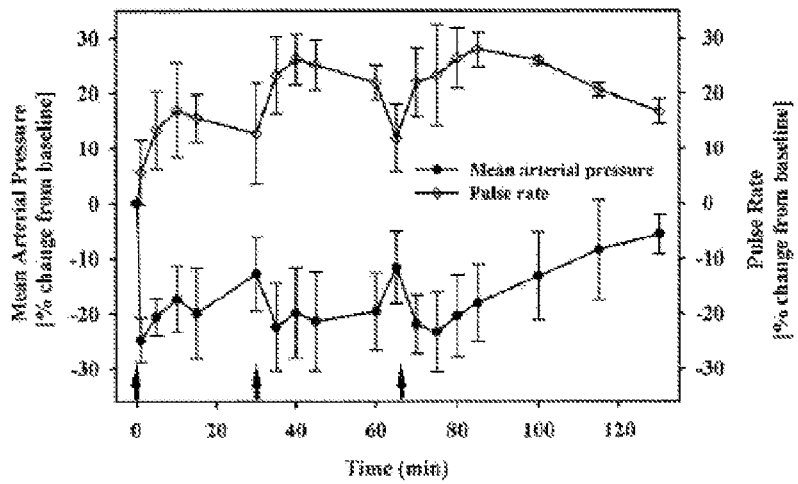

To determine if repeated injections of NO-Cbi were effective, 0.6 nmol NO-Cbi was administered three times to mice at 32 minute intervals, and a decrease in blood pressure and increase in heart rate was observed with each injection (FIG. 4c). Administering 0.8 μmol NO-Cbi repeatedly caused profound hypotension.

Example 14

Figure 5A:
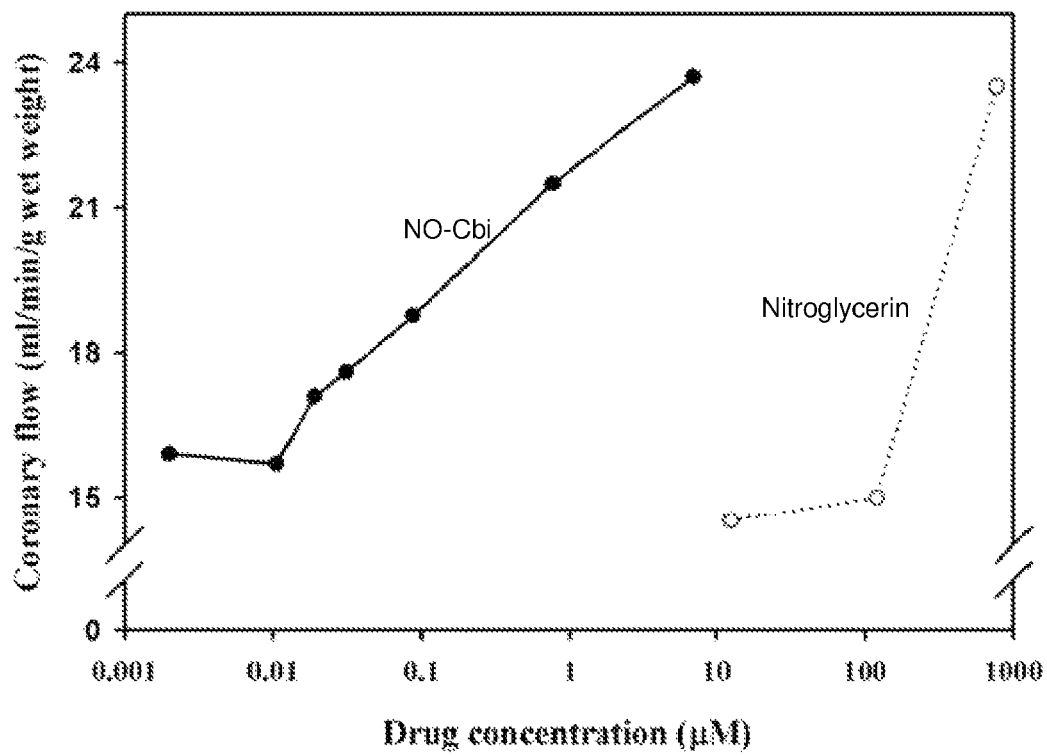
FIG. 5 shows the effect of NO-Cbi on coronary blood flow in isolated mouse hearts and on mouse aortic ring relaxation. Hearts and aortas were removed from NIH Swiss mice anesthetized with sodium nembutal, and coronary flow was measured in the hearts using a Langendorff preparation (FIG. 5a) and relaxation of aortic rings was measured after inducing constriction of the rings with prostaglandin F2α (FIG. 5b). The hearts and aortic rings were treated with a range of concentrations of NO-Cbi (filled circles), nitroglycerin (open circles, dotted line, FIG. 5a), and sodium nitroprusside (open circles, FIG. 5b). Coronary flow was measured on the same hearts for both NO-Cbi and nitroglycerin after an appropriate wash-out period between drugs, and aortic ring relaxation was measured on two rings from the same aorta for NO-Cbi and sodium nitroprusside. The data are the mean of two independent experiments performed on two separate hearts in each experiment (FIG. 5a), and the mean±SEM of two independent experiments performed on three separate aortic rings in each experiment (FIG. 5b).

Effect of NO-Cbi on Coronary Flow in Isolated Mouse Hearts and on Mouse Aortic Ring Relaxation Coronary flow was measured in isolated perfused mouse hearts in a Langendorff system, and was 10.8±0.5 ml/min/g wet weight (n=7 hearts) under basal conditions. Infusing 12.0 μM nitroglycerin into the hearts increased coronary flow 34% to 15.3±1.0 ml/min/g wet weight, while infusing 7 μM NO-Cbi increased coronary flow more than two-fold to 22.8±1.2 ml/min/g wet weight. The latter value is similar to maximal coronary flow of 24.6±1.8 ml/min/g wet weight obtained with 62 μM adenosine. For nitroglycerin to increase coronary flow to that of NO-Cbi, the nitroglycerin concentration had to be increased to 770 μM, or about 100-fold greater than the NO-Cbi concentration (FIG. 5a). NO-Cbi concentrations as low as 20 nM significantly increased coronary flow.

Figure 5B:
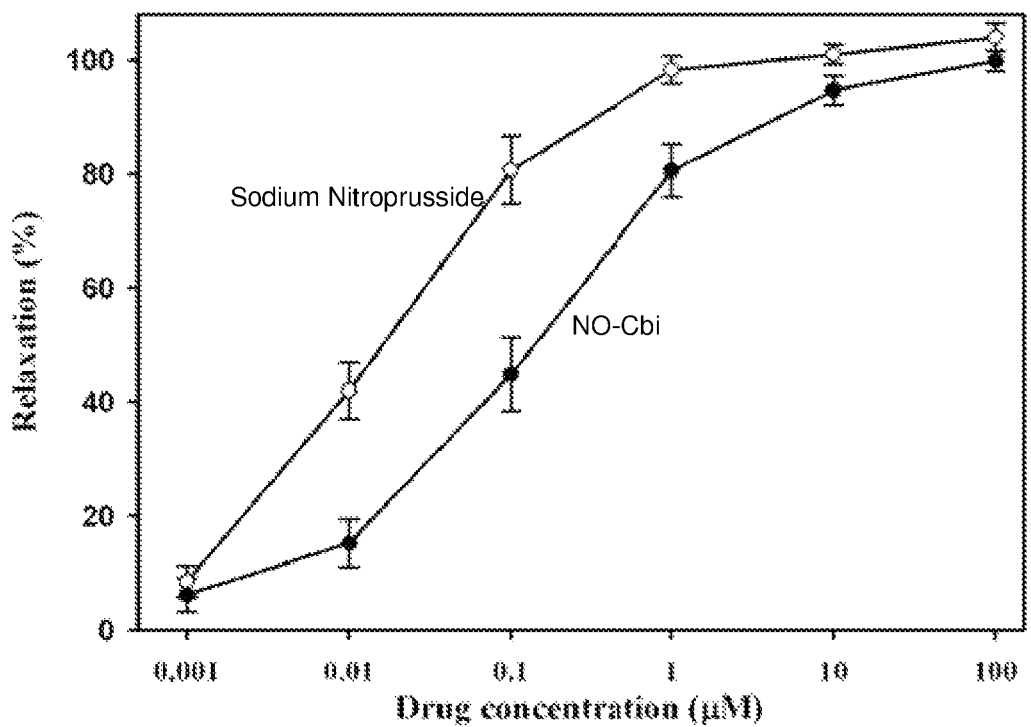

Relaxation of aortic contraction was measured in 3 mm rings cut from thoracic aortas of mice; the rings were pretreated with 2 μM prostaglandin F2α to produce 0.5-1 g of active tension. Both sodium nitroprus side and NO-Cbi induced relaxation of the aortic rings, with nitroprusside being more effective than NO-Cbi in this system: the EC50 values, i.e., the concentrations that induced half-maximal relaxation, were 31±7 nM and 195±12 nM for nitroprusside and NO-Cbi, respectively (FIG. 5b).

Example 15

Effect of NO-Cbi in Rabbits Receiving No Other Treatment

Continuous intravenous NO-Cbi infusions were performed in anesthetized rabbits with systemic hemodynamic monitoring, continuous gas exchange analysis, and diffuse optical spectroscopy (DOS) and continuous wave near-infrared spectroscopy monitoring. DOS monitoring was over muscle as a representation of peripheral tissue, and continuous wave spectroscopy was over muscle and brain region. Six animals have been studied to date, varying NO-Cbi infusion rates in each animal between 1.7 and 6.9 μg/kg/min (1.6 and 6.7 nmol/kg/min).

Figure 6:
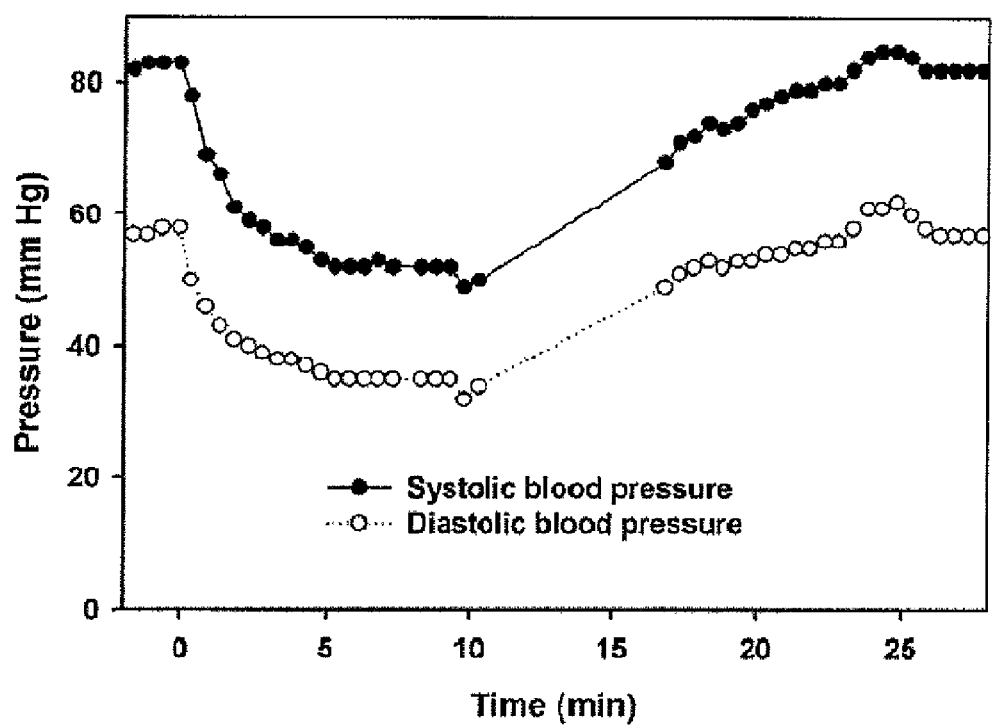
FIG. 6 shows the effect of NO-Cbi on rabbit blood pressure. NO-Cbi was given by intravenous infusion at a dose of 5 μg/kg/min (4.8 nmol/kg/min) to a 3.5 kg rabbit. The infusion was started at zero time, and within 15 sec the rabbit's systolic and diastolic blood pressures began to decrease until they reached a new steady-state at 5 minutes. The infusion was stopped at 10 minutes, but, because of drawing blood through the arterial line for blood gas analysis, the first measurement of blood pressure occurred 6 minutes later. Full recovery required 12 minutes, but it is possible that the initial rate of recovery was faster than shown in the graph. A small overshoot occurred in both systolic and diastolic blood pressure, before returning to pre-treatment levels.

The blood pressure of rabbits is similar to that of humans, but because of anesthesia, initial blood pressures in the rabbits were on average ~80/60 mm Hg (FIG. 6). NO-Cbi caused a marked infusion-rate-dependent decrease in blood pressure within seconds of starting the infusion (FIG. 6). Blood pressure returned to baseline within 12 minutes of stopping the infusion, and starting and stopping the infusion repeatedly yielded similar results. The relatively rapid return of blood pressure suggests a short physiological half-life of NO-Cbi, on the order of 5-6 minutes. The rabbits' heart rate did not change significantly, despite a marked fall in blood pressure, suggesting the NO released from NO-Cbi had a negative chronotropic effect, differing from mice, and perhaps more similar to what will occur in humans. Continuous gas exchange monitoring showed decreased end tidal $CO_2$ and increased arterial-venous oxygen differences, indicating decreased oxygen delivery to tissues. Cardiac output, as measured by the direct Fick method, decreased secondary to the decreased heart rate and likely decreased venous return (Kondo H et al. (1980) Proc. Natl. Acad. Sci. U.S.A. 77:817-821). The effects of NO-Cbi on blood pressure were more rapid and pronounced than those with equimolar amounts of nitroprusside, suggesting nitroprusside may have to undergo some type of biotransformation to release NO.

Figure 7:
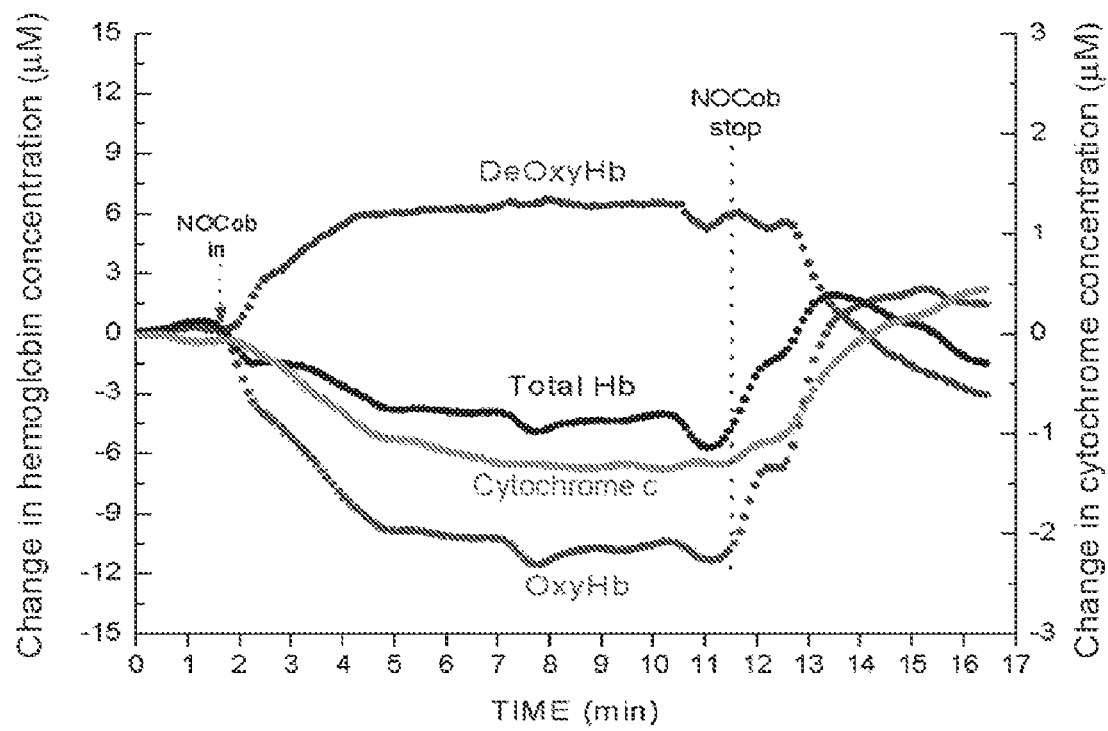
FIG. 7 shows the effect of NO-Cbi on oxy- and deoxyhemoglobin, total hemoglobin, and cytochrome c oxidase in peripheral muscle. NO-Cbi at a dose of 5 μg/kg/min (4.8 nmol/kg/min) was given to a 4 kg rabbit starting at 2 minutes and ending at 11.5 minutes; the drug's effect was monitored by diffuse optical spectroscopy (DOS) over the left thigh muscle. Within seconds of starting the infusion, the deoxyhemoglobin (DeOxyHb) concentration began to increase and the oxyhemoglobin (OxyHb) concentration began to decrease. Total tissue hemoglobin (Total Hb) showed a small decrease, and cytochrome c oxidase (Cytochrome c) became more reduced. All of these changes reversed within 1 minute of stopping the NO-Cbi with a small overshoot in both the oxy- and deoxyhemoglobin concentrations.
Figure 8:
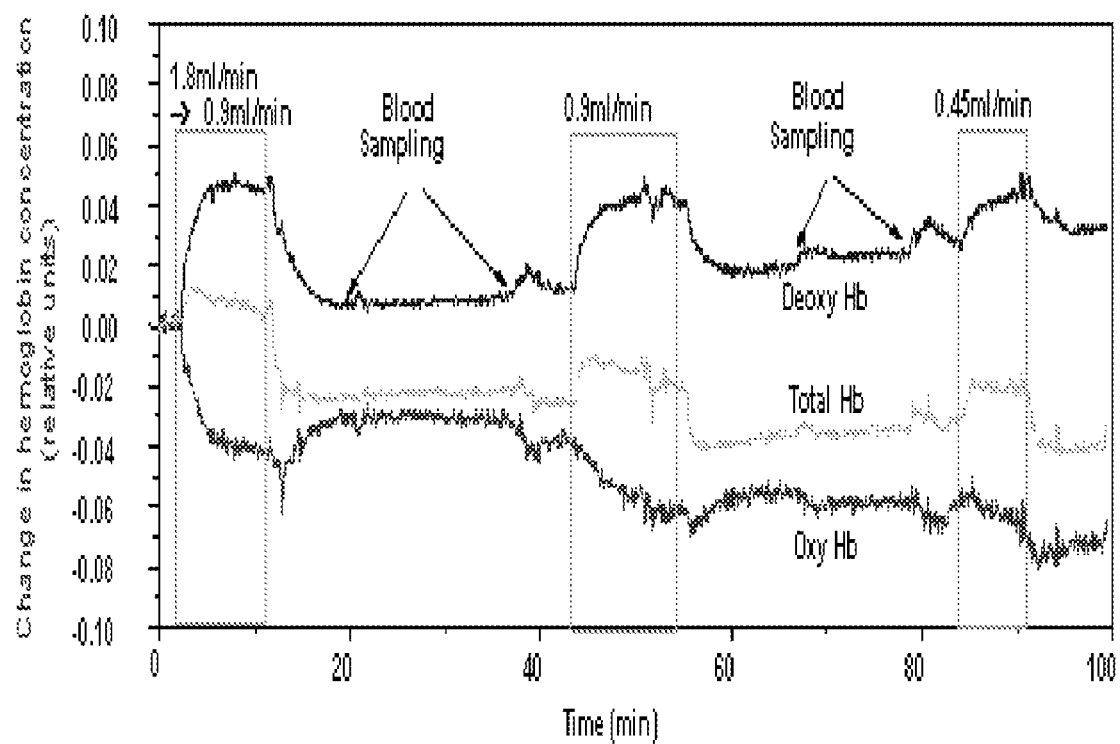
FIG. 8 shows the effect of NO-Cbi on oxy- and deoxyhemoglobin, total hemoglobin, and cytochrome c oxidase in the brain. NO-Cbi was given to a 3.9 kg rabbit at doses of 6.87, 3.44, and 1.72 μg/kg/min (6.6, 3.3, 1.7 nmol/kg/min), as indicated in the brown rectangular boxes corresponding to drug infusion rates of 1.8, 0.9, and 0.45 ml/min, respectively. Infusion times were for 10 minutes, followed by a 20 minute wash-out period. Oxy-, deoxy- and total hemoglobin concentrations were monitored in the brain by continuous wave near-infrared spectroscopy; changes in hemoglobin concentration are shown as relative units, because continuous wave spectroscopy is not quantitative due to light loss from scattering. As occurred in peripheral muscle (FIG. 7), NO-Cbi caused the deoxyhemoglobin concentration to increase and the oxyhemoglobin concentration to decrease. However, contrary to muscle, total tissue hemoglobin showed a small increase, rather than decrease, consistent with CNS autoregulation increasing blood flow in the face of systemic hypotension. The gradual decrease in total hemoglobin over time was from blood sampling for blood gases and blood hemoglobin content. A dose response effect of NO-Cbi on all three hemoglobin concentration changes can be seen.

In both brain and muscle, NO-Cbi decreased tissue oxyhemoglobin concentrations and increased deoxyhemoglobin concentrations, causing a decrease in hemoglobin oxygen saturation: FIG. 7 shows DOS recordings over muscle and FIG. 8 shows continuous wave recordings over brain.

The NO-Cbi-induced changes are consistent with decreased tissue perfusion (presumably from decreased cardiac output), and increased tissue oxygen extraction and venule dilatation. Total tissue hemoglobin decreased slightly in muscle and increased slightly in brain; the decrease in muscle is consistent with decreased tissue perfusion, and the increase in brain was likely from central nervous system autoregulation of blood flow trying to compensate for the decreased cardiac output. Further evidence of reduced tissue perfusion was a decrease in oxidized cytochromes and an increase in reduced cytochromes, decreasing the cytochrome redox state (FIG. 7). Overall, the data suggest NO-Cbi induced both arterial and venule dilatation, and the decrease in hemoglobin oxygen saturation likely occurred because of the profound hypotension.

Example 16

Effect of NO-Cbi in Rabbits Receiving Phenylephrine

Figure 9:
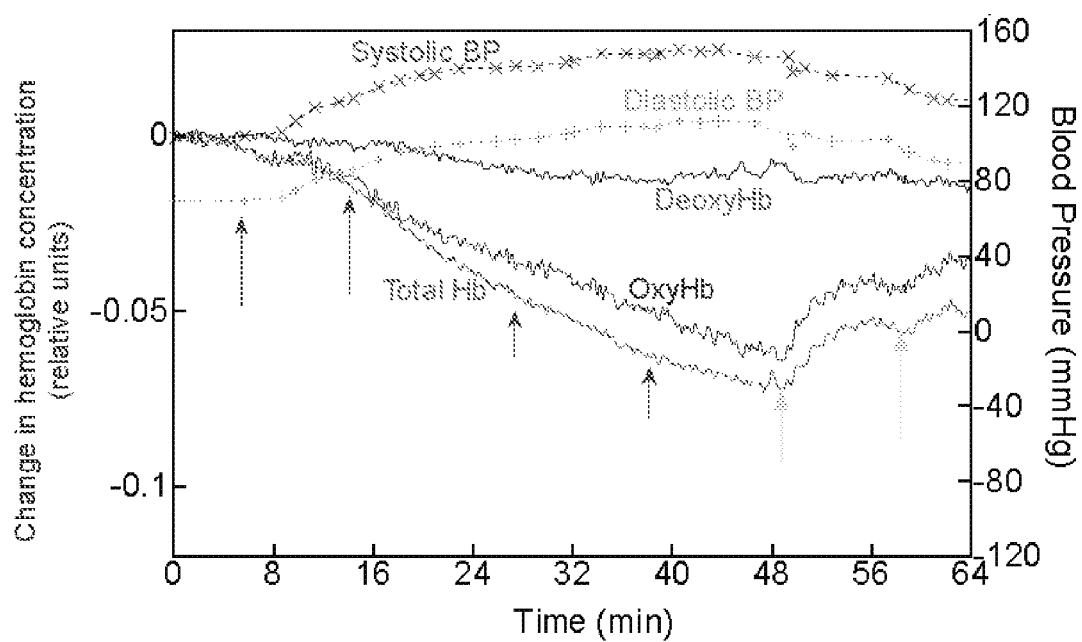
FIG. 9 shows the effect of NO-Cbi on oxy- and deoxyhemoglobin concentrations in rabbits receiving phenylephrine. Phenylephrine was given by continuous intravenous infusion to an anesthetized rabbit at increasing rates from 5 to 20 μg/kg/min; the rabbit remained on the highest phenylephrine infusion rate until the end of the experiment (darker arrows with "A"-shaped arrowheads indicate start times of each increasing dose). At 49 minutes, an infusion of NO-Cbi was started at a rate of 3 μg/kg/min (2.9 nmol/kg/min), with the infusion rate doubled at 58 minutes (lighter arrows with triangular-shaped arrowheads indicate start times of infusions). Systolic and diastolic blood pressure recordings from an intra-arterial catheter are shown. Changes in total hemoglobin, oxyhemoglobin, and deoxyhemoglobin concentrations were measured by continuous wave near-infrared spectroscopy over the left thigh muscle. Phenylephrine caused a progressive decrease in total hemoglobin and oxyhemoglobin concentrations, which reversed within seconds of starting the NO-Cbi infusion.

Decreased tissue oxygenation as occurred in the experiments shown in FIGS. 7 and 8 would clearly be an undesirable effect of treating hypertensive patients with NO-Cbi. However, lowering blood pressure of a hypertensive patient is very different from lowering blood pressure of a normotensive subject, and the experiments described in Example 15 rabbits with normal or low (due to anesthesia) blood pressure. To simulate a hypertensive state, the blood pressure of rabbits was raised using a continuous intravenous infusion of phenylephrine, a peripheral vasoconstrictor (FIG. 9). As the rabbit's blood pressure increased above normal, tissue perfusion and oxygenation decreased, as evidenced by a decrease in total hemoglobin and oxyhemoglobin concentrations in muscle. Serial increases in the phenylephrine infusion rate increased the systolic and diastolic blood pressure, and decreased total hemoglobin and oxyhemoglobin in the muscle.

Within seconds of starting an NO-Cbi infusion, the rabbit's blood pressure began to decrease, and total tissue hemoglobin and oxyhemoglobin concentrations increased; the rabbit continued to receive phenylephrine throughout the NO-Cbi infusion. Thus, in an animal with drug-induced hypertension, NO-Cbi improved tissue perfusion and oxygenation as it lowered blood pressure.

Example 17

Effect of Oral HO-Cbi on Rabbit Blood Pressure

Figure 10A:
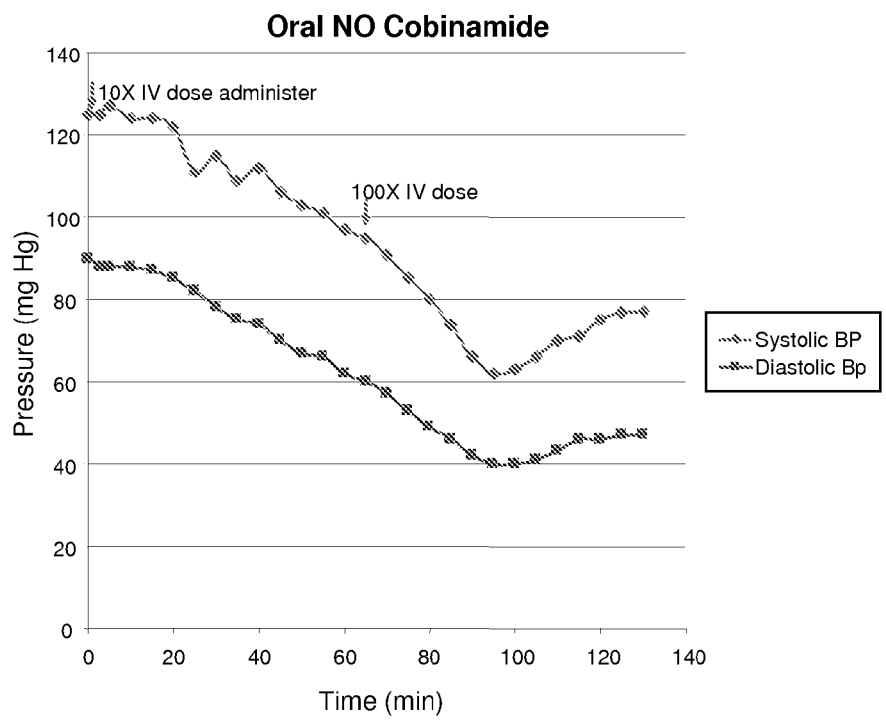
FIG. 10a shows the change in blood pressure after administration of NO-Cbi at 10 and 100 times the intravenous dose used.
Figure 10B:
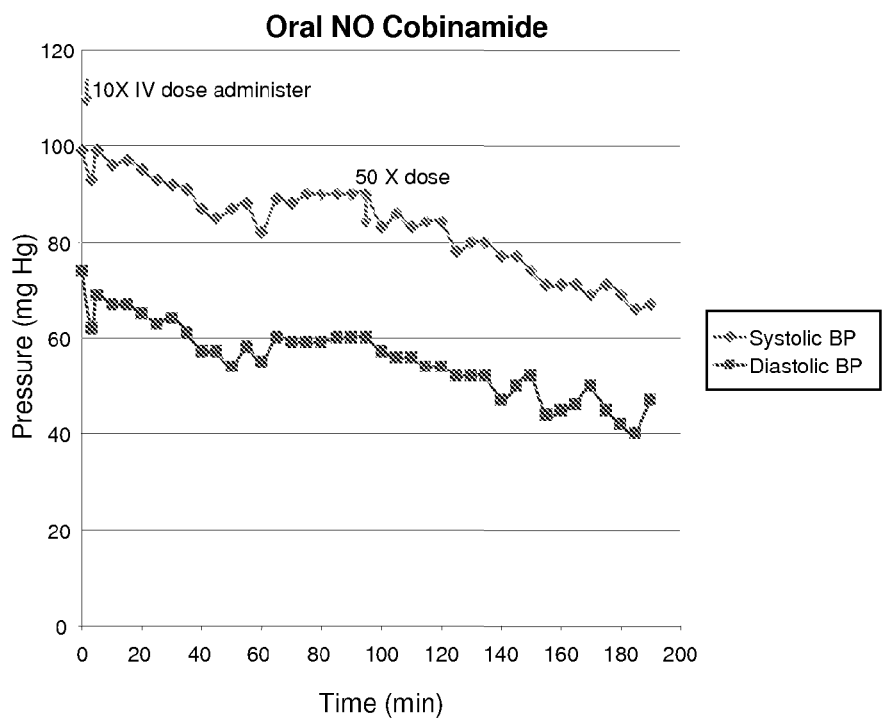
FIG. 10b shows the change in blood pressure after administration of NO-Cbi at 10 and 50 times the intravenous dose used.

An anesthetized New Zealand white rabbit was given NO-Cbi via a nasogastric tube at 10 and 100 (0.32 and 3.2 mg/kg) (FIG. 10a) or 10 and 50 (0.32 and 1.6 mg/kg) (FIG. 10b) times the dose used intravenously. Blood pressure was monitored continuously by an intra-arterial catheter, and was recorded every 5 minutes. The blood pressure was allowed to stabilize for 10 minutes prior to administering NO-Cbi. As FIG. 10 illustrates, the blood pressure began to decrease within 10 minutes of giving the low dose, and showed a steeper decrease on giving the higher dose. The effect of the drug lasted for at least 40 minutes after each dose, and, although the blood pressure showed some increase after 100 minutes (FIG. 10a) or 180 minutes (FIG. 10b), it remained lower than baseline.

All publications and patent applications cited in this specification are herein incorporated by reference in their entirety for all purposes as if each individual publication or patent application were specifically and individually indicated to be incorporated by reference for all purposes.

Although the foregoing invention has been described in some detail by way of illustration and example for purposes of clarity of understanding, it will be readily apparent to one of ordinary skill in the art in light of the teachings of this invention that certain changes and modifications can be made thereto without departing from the spirit or scope of the appended claims.

What is claimed:
1. A pharmaceutical composition comprising a pharmaceutically acceptable carrier and a compound having the formula I:

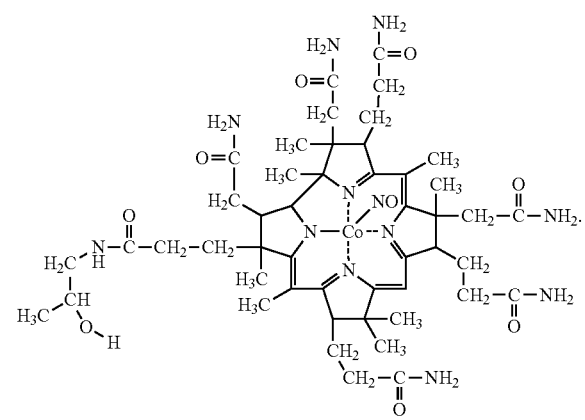

2. A method for treating hypertension in a subject in need of such treatment, comprising administering to the subject a composition comprising a pharmaceutically acceptable carrier and the compound of claim 1 in an amount effective to treat hypertension in the subject.

3. The method of claim 2, wherein the subject is a mammal.

4. The method of claim 3, wherein the mammal is a human.

5. A method for preparing nitrosyl-cobinamide comprising;
deoxygenating cobinamide to produce a deoxygenated cobinamide, reducing the deoxygenated cobinamide with a weak reducing agent to produce a reduced cobinamide, saturating the reduced cobinamide with NO, and removing unreacted NO.

6. The method of claim 5, wherein the weak reducing agent is deoxygenated ascorbic acid.

7. The method of claim 2, wherein the pharmaceutical composition of claim 1 is co-administered with another therapeutic agent.

8. The method of claim 7, wherein the therapeutic agent is administered before the pharmaceutical composition of claim 1.

9. The method of claim 7, wherein the said therapeutic agent is administered simultaneously with the pharmaceutical composition of claim 1.

10. The method of claim 7, wherein the said therapeutic agent is administered after the pharmaceutical composition of claim 1.

* * * * *

UNITED STATES PATENT AND TRADEMARK OFFICE
CERTIFICATE OF CORRECTION

| | | |
|---|---|---|
| PATENT NO. | : 8,222,242 B2 | Page 1 of 1 |
| APPLICATION NO. | : 12/595799 | |
| DATED | : July 17, 2012 | |
| INVENTOR(S) | : Gerry Boss et al. | |

It is certified that error appears in the above-identified patent and that said Letters Patent is hereby corrected as shown below:

Col. 1, lines 5-7

The Government Support clause should be corrected as stated below

--GOVERNMENT SUPPORT

This invention was made with government support under Grant No. AI064368 awarded by the National Institutes of Health. The government has certain rights in the invention.--

Signed and Sealed this
Thirtieth Day of October, 2012

David J. Kappos
*Director of the United States Patent and Trademark Office*

UNITED STATES PATENT AND TRADEMARK OFFICE
CERTIFICATE OF CORRECTION

PATENT NO. : 8,222,242 B2  
APPLICATION NO. : 12/595799  
DATED : July 17, 2012  
INVENTOR(S) : Gerry Boss et al.

It is certified that error appears in the above-identified patent and that said Letters Patent is hereby corrected as shown below:

Title page, item (60), please add the following under the "Prior Publication Data" section on the cover of the patent:

--Related U.S. Application Data

Provisional Application No. 60/911,667, filed on April 13, 2007.--

Signed and Sealed this  
Nineteenth Day of February, 2013

Teresa Stanek Rea  
*Acting Director of the United States Patent and Trademark Office*